(12) United States Patent
Naimark et al.

(10) Patent No.: US 10,018,469 B2
(45) Date of Patent: Jul. 10, 2018

(54) METHOD FOR TERRAIN MAPPING AND PERSONAL NAVIGATION USING MOBILE GAIT ANALYSIS

(71) Applicant: BAE Systems Information and Electronic Systems Integration Inc., Nashua, NH (US)

(72) Inventors: Leonid Naimark, Brookline, MA (US); Yunbin Deng, Westford, MA (US); Geoffrey S. Meltzner, Natick, MA (US); Yu Zhong, Winchester, MA (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 0 days.

(21) Appl. No.: 15/187,900

(22) Filed: Jun. 21, 2016

(65) Prior Publication Data
US 2017/0363427 A1    Dec. 21, 2017

(51) Int. Cl.
  *G01C 21/16* (2006.01)
  *G01C 22/00* (2006.01)
  (Continued)

(52) U.S. Cl.
  CPC .......... *G01C 21/165* (2013.01); *A61B 5/0022* (2013.01); *A61B 5/112* (2013.01);
  (Continued)

(58) Field of Classification Search
  CPC ... G01C 21/165; A61B 5/0022; A61B 5/1112; A61B 5/112; A61B 5/4836; A61B 5/486;
  (Continued)

(56) References Cited

U.S. PATENT DOCUMENTS

| 8,150,624 B2* | 4/2012 | Berardi ................. A61B 5/1112 701/472 |
| 8,753,275 B2 | 6/2014 | Najafi et al. |

(Continued)

FOREIGN PATENT DOCUMENTS

WO   PCT/US2008/000928      1/2008

OTHER PUBLICATIONS

Foxlin, "Pedestrian tracking with shoe-mounted inertial sensors," IEEE Computer Graphics and Applications, vol. 25, No. 6, Nov.-Dec. 2005, pp. 38-46.*

(Continued)

*Primary Examiner* — Todd Melton
(74) *Attorney, Agent, or Firm* — Davis & Bujold, PLLC; Scott J. Asmus (57) ABSTRACT

A method of using signal processing representations from IMU/INS devices to identify terrain types. Using orientation and pace invariant gait dynamics images (GDIs) to identify terrain types. Utilizing signal processing representations from IMU/INS devices to determine relative position in GPS-denied areas. Using orientation and pace invariant gait dynamics images (GDIs) to determine relative position in GPS-denied areas. A method of using signal processing representations from IMU/INS devices to determine absolute position using GDI terrain IDs. A method of using signal processing representations from IMU/INS devices to identity position relative to land classes. Using orientation and pace in variant gait dynamics images (GDIs) to identity position relative to land classes.

19 Claims, 7 Drawing Sheets

(51) Int. Cl.
*A61B 5/11* (2006.01)
*A61B 5/00* (2006.01)
*G06F 17/30* (2006.01)
*G01S 19/10* (2010.01)

(52) U.S. Cl.
CPC ............ *A61B 5/1112* (2013.01); *A61B 5/486* (2013.01); *A61B 5/4836* (2013.01); *A61B 5/6804* (2013.01); *G01S 19/10* (2013.01); *G06F 17/30241* (2013.01); *A61B 2562/0219* (2013.01)

(58) Field of Classification Search
CPC .......... A61B 5/6804; A61B 2562/0219; G01S 19/10; G06F 17/30241
See application file for complete search history.

(56) References Cited

U.S. PATENT DOCUMENTS

| | | | |
|---|---|---|---|
| 9,060,714 | B2 | 6/2015 | Bajcsy et al. |
| 2010/0131228 | A1* | 5/2010 | Huang ................. A61B 5/1112 702/141 |
| 2013/0029681 | A1* | 1/2013 | Grokop ................. G01C 21/16 455/456.1 |

OTHER PUBLICATIONS

Alzantot et al., "UPTIME: Ubiquitous pedestrian tracking using mobile phones," 2012 IEEE Wireless Communications and Networking Conference (WCNC), 2012, pp. 3204-3209.*

Zhang et al., "A Handheld Inertial Pedestrian Navigation System With Accurate Step Modes and Device Poses Recognition," IEEE Sensors Journal, vol. 15, No. 3, Mar. 2015, pp. 1421-1429.*

J. Manty Jarvi, J. Himberg, and T. Seppanen, Recognizing human motion with multiple acceleration sensors, Systems, Man, and Cybernetics, 2001 IEEE International Conference, pp. 747-752, vol. 2, http://ieeexplore.ieee.org/xpl/articleDetails.jsp?tp=&arnumber=973004&queryText%3DRecognizing+human+motion+with+multiple D+acceleration+sensors%2C+ 2001.

J. Manty Jarvi, M. Lindholm, E. Vildjiounaite, S.-M. Makela, H. Ailisto, Identifying users of portable 2 devices from gait pattern with accelerometers, Acoustics, Speech, and Signal Processing, 2005 IEEE International D Conference, pp. 973-976, vol. 2, http://ieeexplore.ieee.org/document/1415569/.

J. Frank, S. Mannor, J. Pineau, and D. Precup, Time Series Analysis Using Geometric Template Matching, 3 Pattern Analysis and Machine Intelligence, Mar. 2013, IEEE Transactions, pp. 740-754, vol. 35, Issue 3, D http://ieeexplore.ieee.org/xpl/articleDetails.jsp?arnumber=6205761.

S. Sprager and M. Juri, Inertial Sensor-based Gait Recognition: A review, MDPI, Sep. 2, 2015, http://www.ncbi.nlm.nih.gov/pmc/articles/PMC4610468/.

C. Mims, Smart Phones that Know their Users by How they walk, Technology Review, Sep. 16, 2010, https://www.technologyreview.com/s/420835/smart-phones-that-know-their-users-by-how-they-walk.

D. Storm, Biometrics: Dream come true or nightmare?, Mar 3, 2011, http://www.computerworld.com/article/2470679/endpoint-security/biometrics--dream-come-tru-or-nightmare?.

Gait Analysis, Wikipedia, https://en.wikipediia.org/wiki/Gait_analysis, accessed Apr. 29, 2016.

J. Boyd and J. Little, Biometric Gait Recognition, Biometrics School 2003, LNCS 3161, pp. 19-42, 2005.

Vishal M. Patel, Rama Chellappa, Deepak Chandra, and Brandon Barbello, Continuous User Authentication on Mobile Devices, IEEE Signal Processing Magazine, 2016.

Yu Zhong, Yunbin Deng, Sensor orientation invariant mobile gait biometrics, 2014 IEEE International Joint Conference on Biometrics (IJCB).

Yu Zhong, Yunbin Deng, Geoffrey Meltzner, Pace independent mobile gait biometrics, 2015 IEEE 7th International Conference on Biometrics Theory, Applications and Systems (BTAS)).

* cited by examiner

| $I(1,1)$ | $I(2,2)$ | $I(3,3)$ | $I(4,4)$ | $\cdots$ | $I(n-2,n-2)$ | $I(n-1,n-1)$ | $I(n,n)$ |
| $I(1,2)$ | $I(2,3)$ | $I(3,4)$ | $I(4,4)$ | $\cdots$ | $I(n-2,n-1)$ | $I(n-1,n)$ | $I(n,n+1)$ |
| $I(1,3)$ | $I(2,4)$ | $I(3,5)$ | $I(4,6)$ | $\cdots$ | $I(n-2,n)$ | $I(n-1,n+1)$ | $I(n,n+2)$ |
| $I(1,4)$ | $I(2,5)$ | $I(3,6)$ | $I(4,7)$ | $\cdots$ | $I(n-2,n+1)$ | $I(n-1,n+2)$ | $I(n,n+3)$ |
| $\vdots$ | $\vdots$ | $\vdots$ | $\vdots$ | | | | |
| $I(1,l-2)$ | $I(2,l-1)$ | $I(3,l)$ | $I(4,l+1)$ | $\cdots$ | $I(n-2,n+l-5)$ | $I(n-1,n+l-4)$ | $I(n,n+l-3)$ |
| $I(1,l-1)$ | $I(2,l)$ | $I(3,l+1)$ | $I(4,l+2)$ | $\cdots$ | $I(n-2,n+l-4)$ | $I(n-1,n+l-3)$ | $I(n,n+l-2)$ |
| $I(1,l)$ | $I(2,l+1)$ | $I(3,l+2)$ | $I(4,l+3)$ | $\cdots$ | $I(n-2,n+l-3)$ | $I(n-1,n+l-2)$ | $I(n,n+l-1)$ |

(a) INNER PRODUCT GDI FOR (a)

Figure 4B

(b) INNER PRODUCT GDI FOR (b)

Figure 4C (c) COSINE SIMILARITY GDI FOR (a)

Figure 4D (c) COSINE SIMILARITY GDI FOR (b)

METHOD FOR TERRAIN MAPPING AND PERSONAL NAVIGATION USING MOBILE GAIT ANALYSIS

FIELD OF THE DISCLOSURE

The present disclosure relates to gait analysis and more particularly to orientation and pace independent mobile gait analysis as used in a variety of applications, including terrain mapping and personal navigation.

BACKGROUND OF THE DISCLOSURE

Cataloging or monitoring surface topology, like on the Earth's surface, can have a variety of applications. This is often referred to as "terrain mapping." A terrain map may be represented in a number of ways and include digital elevation models (DEM), digital terrain models (DTM) and digital surface models (DSM). A terrain map may also be represented by a land class database. Land class databases can fee similar to a DEM in terms of the size of the "pixels" (e.g., each "pixel" could measure several by several meters) however the content of this database is different. For example, one exemplary land class database comprises 13 different land classes. Some of the land classes used in certain embodiments of the disclosure include, grass, wetland, snow, desert, forest, road, urban, agriculture, barren, shrub, water, and rice.

Terrain mapping is useful in health and fitness applications, where the time and distance spent on different terrains may be recorded for use by users and/or health professionals. Due to the dynamic nature of the Earth's terrain a "real-time" terrain map based, in part, on gait analysis would also be advantageous. Terrain mapping may also be useful in location mapping and as a compliment to existing forms of personal navigation.

GPS is a robust and accurate technique for determining location, when a user's receiver has un-occluded reception from multiple satellites; however, in many cases GPS signals are denied. Some examples of GPS-denied areas include indoors, parking garages, tunnels, areas where GPS is occluded by vegetation, zones with skyscrapers, areas when there is a multi-path, and the like. Additionally, there are some areas on earth where adversaries intentionally deny GPS signals by spoofing and jamming. Therefore, alternative to GPS navigation techniques are currently being developed, such as Vision-Aided Navigation. Being able to use a method such as gait analysis for terrain mapping may enable a more complete assessment of a user's location, particularly in GPS-denied areas. This could be beneficial in a number of applications, especially for dismounted infantry, who often operate in mixed outdoor/indoor environments.

Computer vision based approaches to gait analysis extract motion features from image sequences. These approaches are, in general, susceptible to variations in viewing geometry, background clutter, varying appearances, uncontrolled lighting conditions, and low image resolutions. Similarly, measurements from floor pressure sensors have been explored for gait recognition, but cameras or pressure sensors are part of infrastructure, while inertial sensors, as described herein, are worn by an individual. Because no one can install infrastructure over large areas, especially on enemy's territory, a method of personal navigation that does not rely on external infrastructure is needed.

In the past decade, accelerometers have been intensely researched for gait and activity analysis. Such sensors are advantageous compared to both videos and floor sensors for gait analysis. As described above, vision based approaches inter body motion from clattered images. That is highly ambiguous, error prone, and vulnerable to variations in a number of external factors. In contrast, inertial sensors directly measure human body motion to achieve more accurate gait analysis. Inertial sensors are also inexpensive, small in size, and very easy to deploy. Mobile devices such as smart phones and tablets use accelerometers, gyroscopes, and the like to automatically determine the screen layout for improved user experience. In one embodiment of the disclosure, the ubiquity of mobile devices embedded with inertial sensors is used to collect motion data continuously for unobtrusive gait-based authentication and identification.

Typical triple axis accelerometers capture accelerations along three orthogonal axes of the sensor. Given a multivariate time series of the acceleration data, feature vectors are usually extracted for signal windows corresponding to each detected gait cycle or for windows of a pre-specified size. These windows are compared and matched based on template matching, using either the correlation method or dynamic time warping. Alternatively, statistical features including mean, standard deviations, or time span between peaks in windows, histograms, entropy, higher order moments, and features in spatial domain are also used. Fast Fourier Transforms (FFT) and wavelet coefficients in frequency domain are used to compare longer sequences. Classifiers including nearest neighbor classifier, support vector machine (SVM), and Kohonen self-organizing maps have been used. In some cases, preprocessing such as a weighted moving average is applied to suppress the noise in data.

Currently, accelerometers and other inertial sensors only measure local motion where they are worn, and motion patterns differ from one part of the body to another due to the articulated nature of body motion. Even when the sensor is placed at a fixed location, the data measurements can still change depending on the orientation of the sensors. Most existing research has been conducted in controlled laboratory settings to minimize these variations. In some cases, the sensors are placed in a specific way so that intuitive meanings can be assigned to the data components and exploited for gait analysis. As such, existing methods are susceptible to errors when used in real-world conditions. Mobile devices are usually carried in pockets or hands without constraints in orientation. Since the same external motion results in completely different measurements with changing sensor orientation, it is essential to compute an individual's gait independent of sensor rotation for realistic scenarios.

For a mobile device based gait analysis system to succeed in real world applications, such as terrain mapping and personal navigation, it is crucial to address the variations in sensor orientation due to casual handling of mobile devices. It is also crucial to address variation in pace and terrain to accurately use gait analysis in such applications.

SUMMARY OF THE DISCLOSURE

It has been recognized that a need exists for an improved way to use inertial sensors in the field of gait analysis for use in terrain mapping and personal navigation.

One aspect of the present disclosure is a method of determining the position of a user comprising: providing one or more inertial measurement unit (IMU)/inertial navigation systems (INS) devices proximate to a user; collecting data from the one or more IMU/INS devices; creating signal processing representations from IMU/INS data; and determining a relative position of the user.

One embodiment of the method is wherein proximate to a user comprises proximate to a user's wrist or ankle.

One embodiment of the method is wherein creating signal processing representations comprises creating rotation and pace invariant gait dynamics images (GDIs).

One embodiment of the method further comprises comparing a user's position to apriori global coordinates update.

One embodiment of the method further comprises correcting the data from the one or more IMU/INS devices using zero velocity update (ZUPT) methodologies.

One embodiment of the method further comprises coupling the rotation and pace invariant GDIs with a land class database to identify a user's position relative to known land classes.

One embodiment of the method is wherein the position is absolute.

One embodiment of the method further comprises feeding the same IMU data into two processing channels, wherein the first channel comprises ZUPT corrected IMU/INS data for relative positioning and the second channel comprises signal processing representation terrain data for absolute positioning.

One embodiment of the method is wherein the IMU/INS device is embedded in a user's clothing.

One embodiment of the method further comprises communicating the signal processing representations to an operator, where the operator uses the relative position of the user to monitor troop movement.

One embodiment of the method is wherein the determining the relative position of the user comprises using the signal processing representations to determine a transition from a first land class to a second land class.

Another aspect of die present disclosure is a method of tracking an individual on terrain types comprising: providing one or more IMU/INS devices proximate to a user; collecting data from the one or more IMU/INS devices; creating signal processing representations from IMU/INS data; creating a land class descriptor using IMU/INS data from a user; identifying an "on terrain type" signature; and storing the "on terrain type" signature in a database.

One embodiment of the method is wherein proximate to a user comprises proximate to a user's wrist or ankle.

One embodiment of the method is wherein creating signal processing representations comprises creating rotation and pace invariant gait dynamics images (GDIs).

One embodiment of the method further comprises identifying a (latitude, longitude) pair with GPS information; and comparing the GPS information with a land class database.

One embodiment of the method is wherein the land class database comprises land class classifiers comprised of rotation and pace invariant GDIs.

One embodiment of the method is wherein the database is accessed by a health care provider for use in treatment recommendations.

One embodiment of the method is wherein the database is accessed by a user for use in modifying behavior.

One embodiment of the method further comprises communicating the signal processing representations to an operator, where the operator uses the relative position of the user to map an area.

One embodiment of the method is wherein the IMU/INS device is embedded in a user's clothing.

One embodiment of the method is wherein identifying an "on terrain type" signature comprises assigning a terrain's relative hardness.

These aspects of the disclosure are not meant to be exclusive and other features, aspects, and advantages of the present disclosure will be readily apparent to those of ordinary skill in the art when read in conjunction with the following description, appended claims, and accompanying drawings.

BRIEF DESCRIPTION OF THE DRAWINGS

The foregoing and other objects, features, and advantages of the disclosure will be apparent from the following description of particular embodiments of the disclosure, as illustrated in the accompanying drawings in which like reference characters refer to the same parts throughout the different views. The drawings are not necessarily to scale, emphasis instead being placed upon illustrating the principles of the disclosure.

DETAILED DESCRIPTION OF THE PREFERRED EMBODIMENT

Inertial sensors embedded in mobile devices have shown great potential for non-obtrusive gait analysis by directly capturing a user's characteristic locomotion. Although gait analysis using these sensors has achieved highly accurate results under controlled experimental settings, the robustness of such algorithms in the presence of assorted variations typical in "real world" scenarios remains a major challenge. In this disclosure, a mobile gait analysis algorithm that is insensitive to variability in walking speed, and that exploits invariant mobile gait representations independent of sensor rotation is used for terrain mapping. In certain embodiments. Gait Dynamics Images (GDIs) are used for terrain mapping. In certain embodiments, Gait Dynamics Images (GDIs) are used for personal navigation.

Gait dynamics images (GDIs) are a 2d array where the horizontal axis is for time t and the vertical axis is for time lag l. Each entry encodes the interaction in terms of time lagged self-similarity of the 3d acceleration vectors. Specifically, entry (l,t) in the 2d array is defined as either the inner product or the cosine similarity of the motion measurement at time t with the time lagged signal of lag l, i.e., the measurement at time t+l. As a result, the GDIs are independent of the sensor orientation. Furthermore, as these interactions in GDIs encode both temporal dynamics and the context of gait signals, GDIs are highly discriminative for an individual's gait analysis.

Human locomotion for gait is quasi-periodic by nature. This characteristic is readily indicated in the patterns in GDIs. As the motion measurements approximately repeat themselves due to the quasi-periodic nature of human gait, the time lagged self-similarity responses encoded in a GDI peak when the time lag l reaches a gait cycle. This results in a continuous horizontal path of high intensity across the gait dynamics image where the row index of an entry on the path approximates the length of the local gait cycle.

In certain embodiments, this property of gait dynamics images is used to estimate gait cycles by computing the horizontal path across the gait dynamics image with the maximum sum of responses on the path. Local gait cycle lengths are then extracted from the path and used to normalize the gait dynamics image to a previously specified gait length for pace independent gait matching.

In some embodiments, GDIs are used to estimate instantaneous gait cycles and to rectify the time axis such that gait cycles become constant with respect to the new axis, and unwarp the GDI using the rectified time axis to derive pace-independent gait dynamics images. In certain embodiments of the system of the present disclosure, instantaneous gait cycles can be estimated using inertial sensor data from a casually carried mobile device, or an inertial sensor proximate to a user, as well as 1) prior knowledge of gait cycles, 2) continuity constraints in walking speed as it varies, and 3) the quasi-periodic nature of gait signals under a general energy minimization paradigm. In certain embodiments, the general energy minimization paradigm is a Bayesian interpretation that provides robust gait cycle estimation. In certain embodiments, a dynamic programming approach that efficiently solves the energy minimization problem is used.

Figure 1:
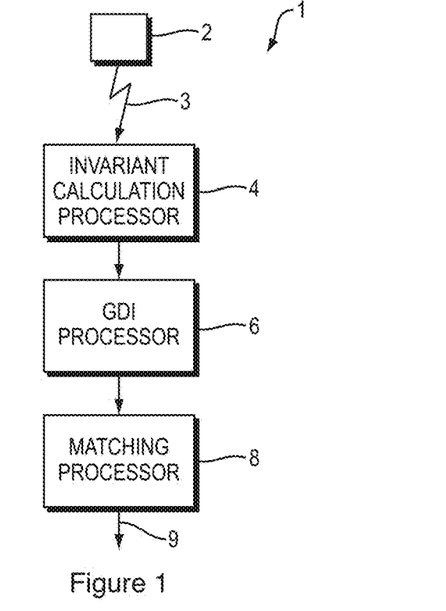
FIG. 1 illustrates one embodiment of a system for determining the gait of an individual.

FIG. 1 illustrates one embodiment of a system 1 where sensors are placed on the belt of the individual. This system includes an inertial sensor 2, an invariant calculation processor 4, a gait dynamics image (GDI) processor 6, and a matching processor 8. The invariant calculation processor 4, as discussed below, calculates invariant values associated with a vector captured by the inertial sensor 2 that are independent of the rotational orientation of the sensor 2. In certain embodiments, the invariant calculation processor 4, calculates invariant values associated with a vector captured by the inertial sensor 2 that are independent of the speed of the individual proximate to the sensor 2. The system may include a wireless link 3 over which the vector is transferred from the inertial sensor 2 to the invariant processor 4. In certain embodiments, the GDI processor 6 generates a gait dynamics image based, at least in part, on the invariant values. In certain embodiments, there is a GDI matching processor 8. This result may be output on output line 9.

"Processor" and "Logic", as used herein, includes but are not limited to hardware, firmware, software and/or combinations of each to perform a function(s) or an action(s), and/or to cause a function or action from another logic, method, and/or system. For example, based on a desired application or needs, logic and/or processor may include a software controlled microprocessor, discrete logic, an application specific integrated circuit (ASIC), a programmed logic device, a memory device containing instructions, or the like. Logic and/or processor may include one or more gaits, combinations of gaits, or other circuit components. Logic and/or a processor may also be fully embodied as software. Where multiple logics and/or processors are described, it may be possible to incorporate the multiple logics and/or processors into one physical logic (or processors). Similarly, where a single logic and/or processor is described, it may be possible to distribute that single logic and/or processor between multiple physical logics and/or processors.

Accelerometers were originally introduced to mobile devices to automatically adjust the screen display layout. The most commonly used 3-axis accelerometers measure accelerations along three orthogonal axes of the sensor. The gravity vector can be computed using these measurements to determine the device orientation. As it turns out, these acceleration measurements also capture the distinguishing locomotion patterns that are characteristics of a user's gait and can be used for navigation. In certain embodiments, the resultant characteristic gait images can also be sued for terrain mapping as described herein.

Figure 2:
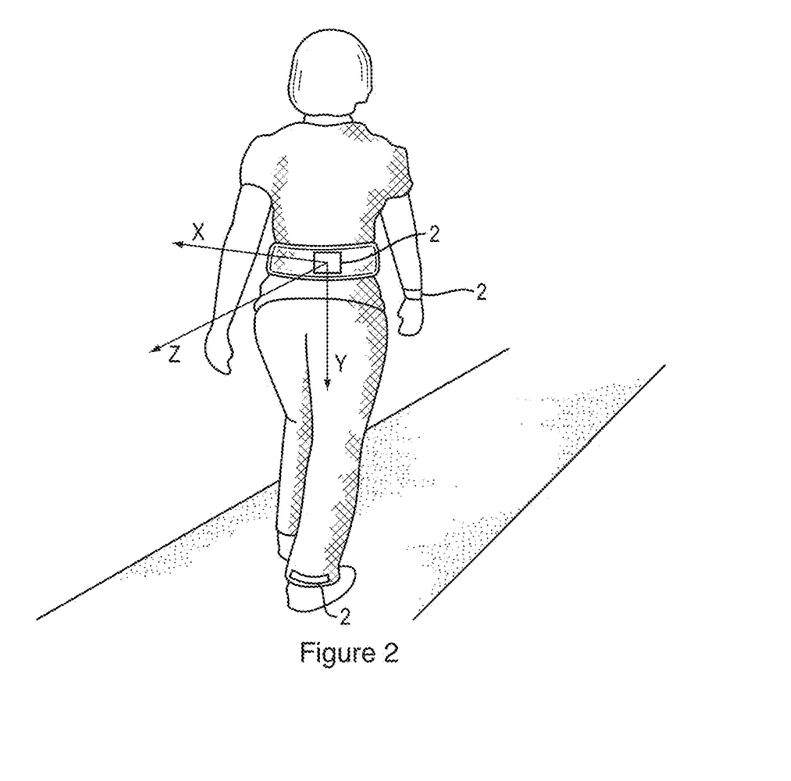
FIG. 2 is an illustration of an inertial sensor being carried by an individual.

FIG. 2 illustrates an example sensor that, in one embodiment, is the inertial sensor 2 of FIG. 1 attached to back of the waist of a person and additionally illustrates orthogonal x, y and z axes. In certain embodiments, one or more inertial sensors 2 may be proximate to the user's wrist. In certain embodiments, one or more inertial sensors may be proximate to the user's ankle. In some embodiments of the method and system of the present disclosure, one or more inertial sensors may be embedded in clothing. In some embodiments, the inertial sensors may be implanted in the user.

According to Applicant's own work, given two 3d acceleration vectors at times $t_1$ and $t_2$, with measurements $\overrightarrow{A(t_1)}=[x(t_1)\ y(t_1)\ z(t_1)]^t$ and $\overrightarrow{A(t_2)}=[x(t_2)\ y(t_2)\ z(t_2)]^t$ by an inertial sensor with reference frame OXYZ, the forces are also captured by a second inertial sensor with a reference frame OX'Y'Z': $\overrightarrow{A'(t_1)}=[x'(t_1)\ y'(t_1)\ z'(t_1)]^t$ and $\overrightarrow{A'(t_2)}=[x'(t_2)\ y'(t_2)\ z'(t_2)]^t$. The rotation between the two sensors is R to give $\overrightarrow{A'(t_1)}=R\overrightarrow{A(t_1)}$ and $\overrightarrow{A'(t_2)}=R\overrightarrow{A(t_2)}$. Although the raw acceleration readings depend on the sensor orientation, it is possible to extract orientation invariant features using a pair of motion vectors at times $t_1$ and $t_2$:

$$\left\langle \overrightarrow{A'(t_1)}, \overrightarrow{A'(t_2)} \right\rangle = \left\langle \overrightarrow{RA(t_1)}, \overrightarrow{RA(t_2)} \right\rangle \quad \text{Equation 1}$$
$$= \overrightarrow{A(t_2)}^T R^T R \overrightarrow{A(t_1)}$$
$$= \overrightarrow{A(t_2)}^T \overrightarrow{A(t_1)}$$
$$= \left\langle \overrightarrow{A(t_1)}, \overrightarrow{A(t_2)} \right\rangle$$

Although the inertial sensor's raw readings depend on the sensor orientation, the inner product between a pair of the 3d measurement vectors do not. The inner product invariant to sensor rotation is defined as:

$$I_{inner}(\overrightarrow{A(t_1)},\overrightarrow{A(t_2)})=\langle\overrightarrow{A(t_1)},\overrightarrow{A(t_2)}\rangle \quad \text{Equation 2:}$$

This invariant quantity is related to the projection of one acceleration vector on the other, which stays the same regardless of the choice of the reference frame. In the special case when $t_1=t_2$, $\langle\overrightarrow{A(t)}, \overrightarrow{A(t)}\rangle=\langle\overrightarrow{A'(t)}, \overrightarrow{A'(t)}\rangle$, and $\|x(t)^2+y(t)^2+z(t)^2\|_{1/x}=\|x'(t)^2+y'(t)^2+z'(t)^2\|^{1/2}$. That is, the magnitude of the 3d acceleration vector is invariant to sensor placement. From these invariants, we can also derive additional invariant features with normalizing effects. Among them is the cosine similarity measure:

$$I_{cos}(\overrightarrow{A(t_1)}, \overrightarrow{A(t_2)}) = \frac{\langle\overrightarrow{A(t_1)}, \overrightarrow{A(t_2)}\rangle}{\|\overrightarrow{A(t_1)}\|\|\overrightarrow{A(t_2)}\|}$$

Equation 3

Intuitively, this invariant is the cosine of the angle between two 3d acceleration vectors. It remains the same for all reference frames that are static with respect to each other. Equation 2 and Equation 3 are also invariant to symmetry transforms of the signals.

In certain embodiments, the invariant motion interactions are exploited to extract features that characterize the locomotion dynamics and which are robust to variations in sensor placement. Given a 3d acceleration time series of size n sampled at regular time intervals $[\overrightarrow{A(1)}, \overrightarrow{A(2)}, \overrightarrow{A(3)}, \ldots, \overrightarrow{A(n-1)}, \overrightarrow{A(n)}]$, a two dimensional matrix called a Gait Dynamics Image (GDI) is created and is used to capture invariant motion dynamics over time and interactions within each gait cycle. GDIs also extend to all linear transforms of the raw acceleration data, including integration over time for velocity and double integration over time for displacement. That is, for Equation 2 and Equation 3 (described above), A(t) can be replaced with any linear transform T(A(t)) of A(t).

The invariant feature is then computed using data vectors $\overrightarrow{A(t_1)}, \overrightarrow{A(t_2)}$ be $I(t_1, t_2)$, using either Equation 2 or Equation 3 (defined above). In certain embodiments, the Gait Dynamics image (GDI) is defined as follows:

$$GDI(t,f)=I(f,t+f-1),$$ Equation 4:

where: t=1, ..., t and f=1, ..., n−t+1
where t is the range of the time delay for concerning pairwise motion interactions. In certain embodiments, context is encoded within a typical gait cycle.

Figure 3:
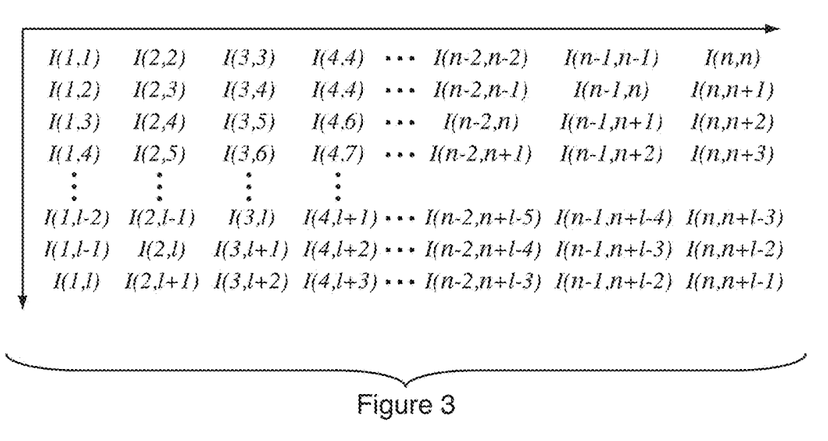
FIG. 3 illustrates a gait dynamics image (GDI) which characterizes flow dynamics over time and interactions within each gait cycle that is independent of the placement of the inertial sensors according one of the embodiments of the present disclosure.
Figure 4A:
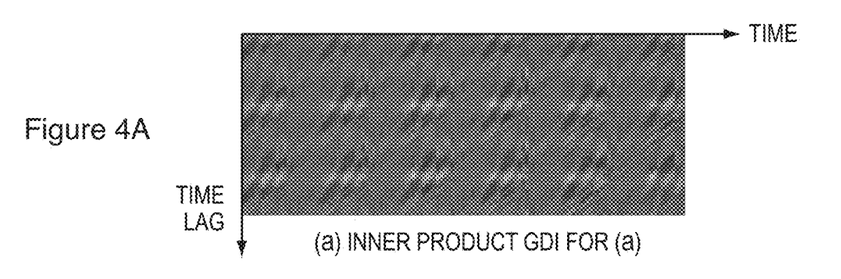
FIG. 4 contains exemplary images of gait dynamics images according to one embodiment of the present disclosure.
Figure 4B:
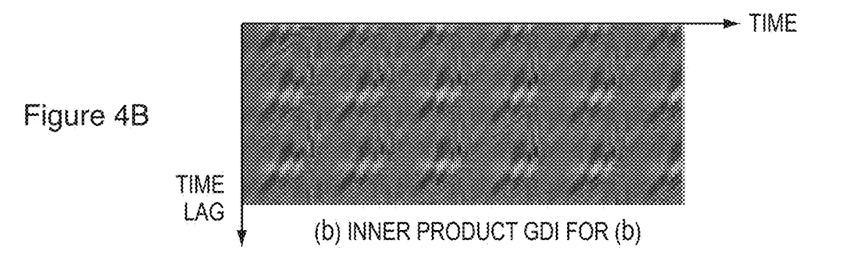
Figure 4C:
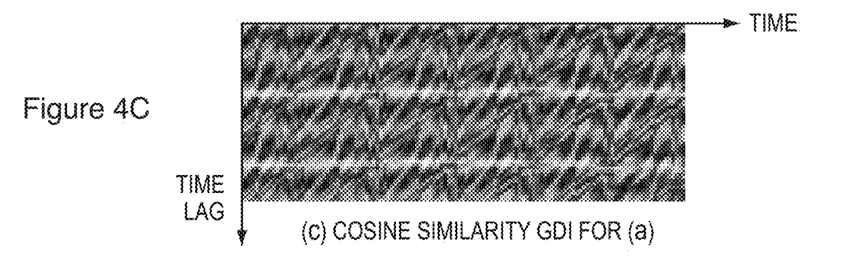
Figure 4D:
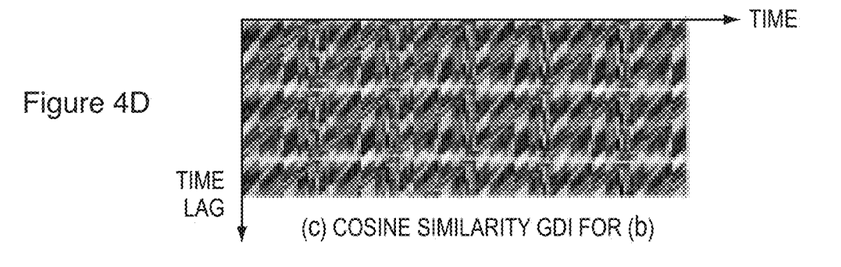

Gait dynamics images encode rich dynamics and context information characterizing the unique gait of an individual. As shown in the ith row (see FIG. 3) of the GDI contains all pairwise interactions of time delay t−1 over time, while the jth column consists of interactions between the motion at time j and all its successors up to time lag 1−1 to capture local context. In particular, the first row of the inner product gait dynamics image, which are the inner products of observation pairs with time lag 0, corresponds to the magnitude sequence that has been shown to be advantageous to the raw component acceleration features in cell phone based gait ID studies, and which has been used in existing research to handle the variations in sensor placement. The remaining rows contain the interactions at varying time lags that contribute to additional discriminating information of the gait dynamics.

The cosine similarity GDIs can be considered a normalized form of the inner product GDIs by taking out the effects of the magnitudes. These GDIs only depend on the angles between the observation vectors. This normalization may improve the robustness to noisy magnitudes in the data. In summary, the GDI, although built on the sensor rotation dependent raw acceleration measurements, achieves a view invariant representation of the governing dynamics in the original multivariate time series for robust gait analysis. Furthermore, it preserves the local interactions and contextual information within each gait cycle essential for discriminative motion analysis to enable highly accurate gait analysis.

Referring to FIG. 4, exemplary gait dynamics images are shown. GDIs encode both dynamics for time series and local interactions. With the irregularly periodic input locomotion time series, gait dynamics images also display quasi-periodicity in both the time and time lag domains with the period approximating the length of a gait cycle.

As shown in the gait dynamic images of FIG. 4, when the time lag coincides with the length of the local gait cycle, the inner product (Equation 2) or normalized correlation (Equation 3) are high as the signals repeat themselves. This is reflected by horizontal lines of high similarity measurements in both GDIs, starting with the first row, repeating at the length of a gait cycle. A bright value at a pixel indicates a high degree of similarity in terms of inner product for the inner product GDIs and normalized correlation for cosine similarity GDIs. Gait cycles can be estimated by fitting smooth horizontal curves across the image which maximizes the overall intensities. Due to the quasi-periodic nature of gait and the repetitive pattern in GDIs, we set l to be a little more than the length of average gait cycles (for example, equal to about 2.5) to preserve all contexts within a gait cycle when computing GDIs.

GDIs show dominant superiority over magnitude features, which have been exploited in other gait analysis methods. In certain embodiments, GDIs are applicable to motion analysis for activity recognition and analysis which would indicate the type of activity in which a person is participating by analyzing collected motion data.

Figure 5:
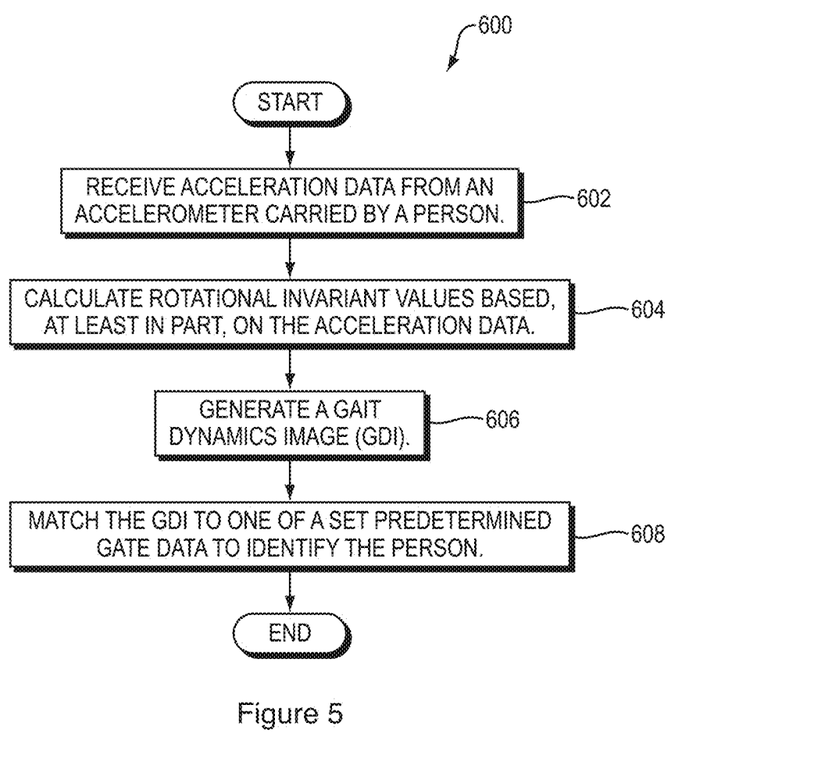
FIG. 5 illustrates one embodiment of a method for identifying the gait of an individual.

FIG. 5 illustrates a method 600 of identifying an individual based on their gait. Acceleration data is received, at 602, from an inertial sensor proximate to a person. The acceleration data corresponds to a gait of the person. Rotational invariant values are calculated based, at least in part, on the acceleration data, at 604. The rotational invariant values are independent of a rotational position of the accelerometer on the person and may be calculated as discussed above. Pace invariant values are calculated based, at least in part, on the acceleration data, at 604. The pace invariant values are independent of the speed of the person's gait and may be calculated as discussed above. A GDI is calculated based, at least in part, on the rotational and pace invariant values.

While for purposes of simplicity of explanation, illustrated methodologies are shown herein and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

In the foregoing description, certain terms have been used for brevity, clarity, and understanding. No unnecessary limitations are to be implied therefrom beyond the requirement of the prior art because such terms are used for descriptive purposes and are intended to be broadly construed. Therefore, the disclosure is not limited to the specific details, the representative embodiments, and illustrative examples shown and described. Thus, this application is intended to embrace alterations, modifications, and variations that fall within the scope of the appended claims.

In certain embodiments, comparing the gait of an individual, or changes in gait over time may aid in rehabilitation. In certain embodiments, gait information may be transmitted to a doctor, such that the doctor can compare past and present gait information for an individual to detect problems and/or use the information to suggest or modify treatment. In certain embodiments, GDIs may be used by individuals to map terrain traveled for use with fitness goals and to assess changes in terrain over time.

In certain embodiments the hardness of a terrain is detected using rotation and pace invariant GDIs. In certain embodiments, GDIs can be used for terrain mapping. In addition to using terrain mapping for health and fitness applications, terrain mapping can help in civilian and military applications as well. In certain embodiments, GDIs can be used to aid in personal navigation in GPS-denied areas. By providing an accurate location, personnel can be kept safe as their location will be known. In certain embodiments, terrain mapping can be used to map an environment or areas where GPS signals are poor or absent. In certain embodiments, terrain mapping using GDIs can help identify and locate first responders. In certain embodiments, a transition from one "land class" to another can be used to pinpoint the location of a user.

In certain embodiments, the system and method for terrain hardness characterization, a subset of terrain mapping, is used as part of personal health monitoring. In certain embodiments, the system comprises inertial sensors, or inertial measurement units (IMUs) in variety of form factors, including but not limited to smart phones, fitness bracelets, watches, and eyewear. In certain embodiments, the system further comprises a standard GPS. In certain embodiments, the method of mapping terrain comprises one of two processes or their combination. For the combination process, the first process is to match GPS coordinates against an exiting land class database and the second process is to match inertial data signatures against personal (small) data sets of terrain and elevation signatures. Whether in combination or using IMUs alone, one of the possible embodiments of the system is to create signatures by using gait dynamic images (GDI).

Recently there has been an increasing interest in both health and fitness tracking applications and devices in consumer market. Typical applications for Smart Phones (for example "MapMyRun", "Pedometer", "MyFitnessPal") actively monitor activities such as walking, running, cycling, etc. Some of the applications require users to select the activity type s/he is going to be engaged in. This is needed, for example, for better calculation of calories burned. Other applications automatically estimate ongoing activity based on GPS and inertial sensors (IMU) feeds without user interaction or even constantly running in background of the device.

Specialized devices (ex. Jawbone UP3, Nike FuelBand SE, Fitbit, Moov) are mostly coming in a form factor of bracelets to provide extended functionality to one of the smart phone apps. The biggest two differentiators are: 1) bracelets do not need to be recharged as often as smartphones (for example Jawbone works for a week without recharge, while Garmin claims their bracelet works for 1 year without recharge); and 2) bracelets are permanently or repeatedly placed into the same parts of the body, therefore they provide better accuracy of activity type assessment and characterization, when such estimation is based on inertial sensors. Bracelets provide more parameters such as activity level, sleeping characteristics, daily calories burned, and the like, since they are supposed to be worn basically all the time.

Since the most common human fitness activity is running/jogging and daily fitness activity is walking, the focus of many apps in both smartphones and bracelets is on detailed characterization of such activities, for example, counting steps. This is done using inertial sensors, and then other characteristics of activity are calculated and provided to the user, usually based on user-provided analysis data and/or GPS feeds.

It is well-known that prolonged walking (and especially running) on harder surfaces such as asphalt and concrete provides higher impact on a runner's joints, causing an extensive wear and potentially creating health problems. The parts of the body that are most affected are knees, ankle/foot, and lower back. Therefore, it would be very useful for the user to know on which surfaces s/he runs/walks and for how long. In certain embodiments, an estimated impact on a user's joints is calculated based on the information collected.

Experienced runners are generally aware of the negative impact on their joints; therefore many of them try to run on unpaved paths or other natural surfaces, when such option is available. However in urban environments, when a runner's workout starts by exiting their home and ends when they return home the mixture of terrains is unavoidable.

Figure 6:
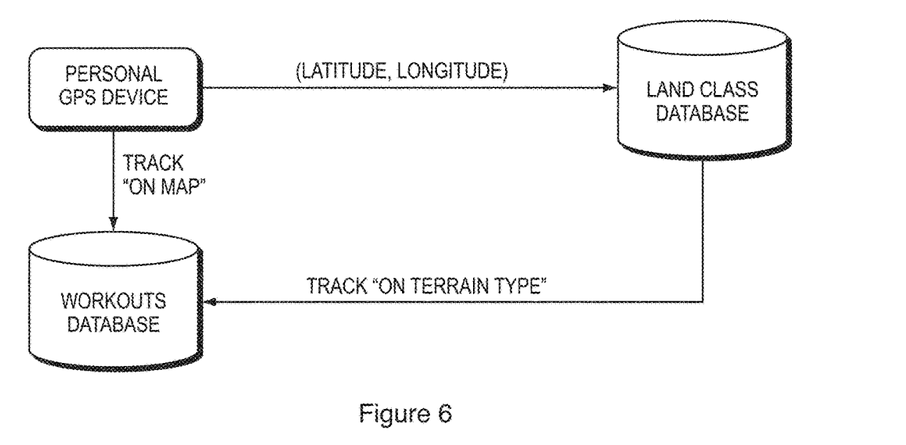
FIG. 6 shows a GPS-based solution according to one embodiment of the present disclosure where a runner's track may be recorded, based, in part, on terrain hardness.

While a GPS-based solution provides a step in the right direction, such a solution is not accurate. Using a modern GPS system with a map labeled by certain terrain types is depicted in FIG. 6. FIG. 6 shows one embodiment of the system of the present disclosure comprising a GPS-based method to record a runner's track, based, in part, on terrain type. A typical GPS system is capable of providing accuracy to within several meters. The conventional use of the GPS system is to create a track "on map" associated with a completed workout and to store that map in a workout database on device or in the cloud. One assumption with such systems is that the land-class database (map) is perfect, or has high resolution data without any errors. This not necessarily the case.

If a person runs on a wide asphalt road, her placement at any time could be uniquely associated with an "asphalt road" terrain type in the map. Similarly, when a person traverses a baseball field, her placement could be associated with a "grass" terrain. However, in many cases (for example, along bike trails) there are sometimes parallel paved and unpaved paths, making GPS location insufficient to determine the type of terrain a person is located on, therefore creating significant uncertainty in track "on terrain type".

Existing, publically available (or GFI) databases are low resolution, with resolution of only about 10-30 meters. These database classes have a significant amount of errors in them, since they are created using clustering and other machine learning techniques on satellite (or ground based) imagery, and such approaches have "built-in" errors. An additional challenge for GPS-based techniques is that such databases become outdated, for instance when new construction occurs or forests or grasslands converted to croplands, and the like.

Figure 7:
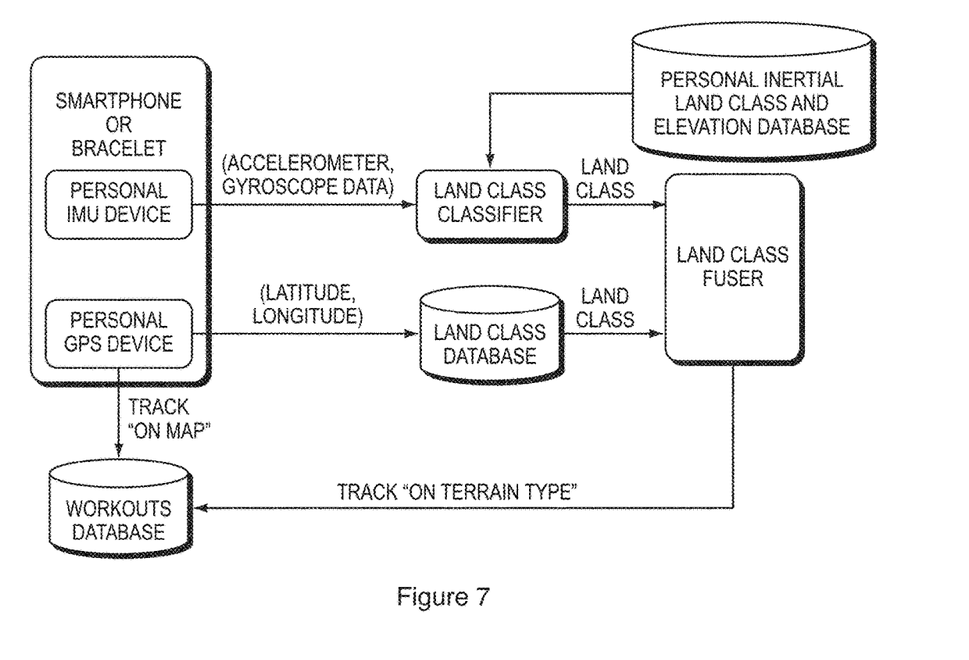
FIG. 7 is a diagram of one embodiment of the present disclosure.

FIG. 7 illustrates the overall processing diagram for one embodiment of the present disclosure. Similar to FIG. 6, a GPS produces a (latitude, longitude) pair, and is compared with an existing land-class database. The output of the Land Class Database block is one of standard land classes (ex. "grass", "paved road", "sand", "wetland"). In certain embodiments, parallel processes use IMU data (e.g., accelerometers, gyroscopes, and the like) to create land class descriptors (signature). In certain embodiments, this signature is compared with personal (or default) signatures that have been previously created.

One embodiment of the present disclosure uses Gait Dynamic Images (GDI) as Land Class Classifiers. Such use of GDIs is beneficial, because GDIs are rotation and pace invariant, and therefore produce much higher detection rates for smartphones, or other inertial sensors proximate to a user, which could be randomly placed in a pocket, bag, or held in a hand or used by different users. The data from stationary devices (worn on the same part of the body at same orientation), like bracelets, watches or waist pedometers could be also processed with alternative to GDIs 1-dimensional signal processing (for example FFT, or wavelets). In certain embodiments, data from two channels is fused in a Land Class Fuser module, which incorporates confidence weights associated with each channel to provide an estimated "terrain type." In certain embodiments, a time stamped terrain type is subsequently stored as Track "on terrain type" into a workout database.

In certain embodiments, land classes include urban and built up areas, water, agriculture, rangeland, forest land, wetlands, bare, tundra, and others. For urban or built-up classes, this can be commercial, industrial, transportation, and communications/utilities in some cases, recreational grasses, such as those that occur in golf courses or parks can be considered urban or non-urban. In some classifications, water can be streams/canals, lakes/ponds, reservoirs, bays, or open marine. Agricultural areas that are herbaceous in nature (cropland and pasture) may be subdivided into classes: pasture/hay, row crops, small grains and fallow. In some systems rangeland is subdivided into grasslands/herbaceous and shrub land classes. Forest land can include evergreen forest, deciduous forest and mixed forest. Clear cut and burned areas are often classed as transitional bare areas. Wetlands may be two classes defined as woody wetlands and emergent/herbaceous wetlands. Bare may have three classes. These are: bare rock/sand clay, quarries/strip mines/gravel pits and transitional bare. While tundra is treated as a distinct class, tundra (including arctic/alpine vegetation) is considered to be either grasslands/herbaceous or shrub land in some systems. In certain embodiments, it is less about what the particular land class is called at a given time, and more about the hardness of the terrain at that particular time.

In certain embodiments, it is important to know when a transition from one land class or terrain type has transitioned to another land class or terrain type. These methods can be used separately, or combined with other location information to find the precise location of a user. In certain embodiments, the method of terrain mapping using gait analysis comprises two parallel processes, both resulting in a land class estimation. These land class estimations are merged by a land class fuser to provide final "terrain type" that are led into a database for later use.

In one example, when a runner/walker completes his or her workout, the database may contain the time and distance she spent on each type of terrain, for example 50% on asphalt and 50% on unpaved clay road. This could be further used, for example, to amend the track for the user's future workouts to include more soft terrain or for any other applications. In certain embodiments, a doctor's office could receive such records to diagnose conditions, modify treatment and/or aid in providing recommendations. In certain embodiments, during the workout itself, the surface hardness can be displayed to an individual to indicate the need to move to a softer surface. In certain embodiments, the information may be transmitted to others who are monitoring the individual's movements.

In certain embodiments, ZUPT (zero velocity update) corrected IMU/INS (inertial measurement unit/inertial navigation system) data are used for relative positioning. In certain embodiments, the position is relative to apriori global coordinates update (e.g., received from GPS, other global navigation system, geo-referenced vision-aided updates). In certain embodiments, Gait Dynamics Images (GDIs) terrain IDs are used for absolute positioning. In some embodiments, GDIs are coupled with a land class database and/or a Digital Elevation Model to identity position relative to land classes.

Figure 8:
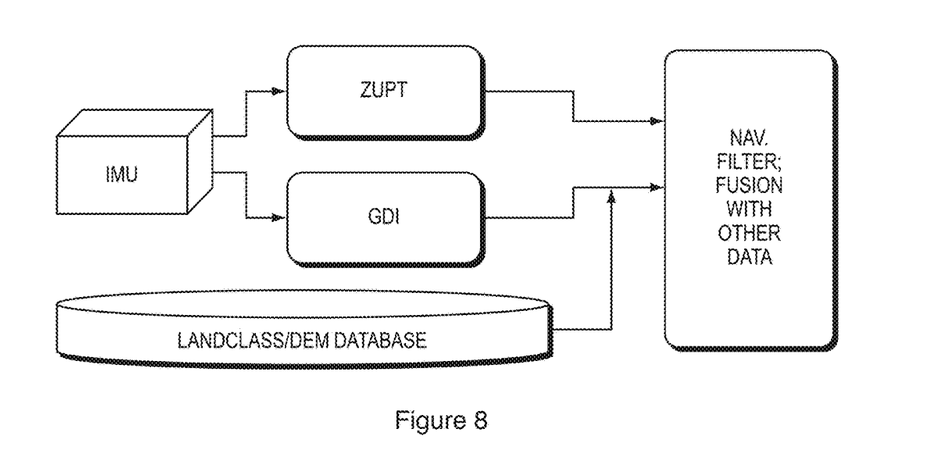
FIG. 8 illustrates the same IMU data fed into two different processing channels according to certain embodiments of the present disclosure.

FIG. 8 illustrates the same IMU data that is fed into two processing channels in one embodiment of the disclosure. The first channel is ZUPT corrected IMU/INS for relative positioning. The second channel is Gait-Dynamics Images (GDIs) terrain ID for absolute positioning in one embodiment of the disclosure. In certain embodiments, GDIs are coupled with a land class database and/or a Digital Elevation Model to identity position. In certain embodiments, an INS/ZUPT+GDIs/terrain solution can be integrated with other modalities for complete GPS-free navigation solution on the level of individual dismount or inside multi-agent navigation system including humans and vehicles.

Figure 9:
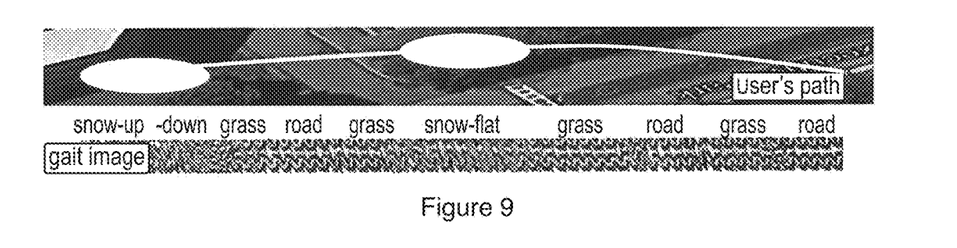
FIG. 9 illustrates the terrain in the top image and collected gait images in the bottom image for one embodiment of the present disclosure.

In certain embodiments of the system and method of using gait analysis for terrain mapping of the present disclosure, wearing bracelets on ankles (anklets) enables an accurate determination of the type of terrain a person is walking/running on. In one study, Applicant showed that a subject wearing a smartphone in a sock (representing an anklet) walked 110 m through 10 terrain segments of grass, asphalt and snow (line track), as shown in FIG. 9. The system detected all 10 terrain transitions in the test. In this example, the transitions included snow to grass to asphalt road to grass to snow to grass to asphalt road to grass to asphalt road. Terrain transitions are indicated in the collected gait image. It is important to note that the gait images for terrain segments of the same type (e.g., the 4 grass segments) were highly correlated with one another.

The top image in FIG. 9 illustrates the terrain in the test. Snow terrain was added to existing Google earth imagery to reflect actual conditions of the walking trade. The bottom image shows collected gait images obtained by Applicant on that terrain. The terrain transitions were readily visible in the gait image. It will be understood that in the train mapping context as used by runners, for example, it is less important what the land class is called, but rather the terrain hardness. In the navigation context, the specific name of the land class is less import than identifying a transition from one land class to another land class as a way of pinpointing location.

In one embodiment, a INS/ZUPT anklet is able to provide 6 m accuracy for up to 4 minutes. Additionally, any terrain crossing detected (as shown in FIG. 9) during this time with GDI improves global position accuracy within less than 1 m and serves as a GPS-like update. In certain embodiments, all possible human movements can be monitored using an additional wrist bracelet. The referenced less than 1 m accuracy might be subject to terrain (land-class) database resolution. To achieve such 1 m accuracy the databases should have also 1 m or better resolution.

Another embodiment of using gait analysis for terrain mapping of the present disclosure aids in personal navigation in GPS-denied environments. Dismounted infantry and squads must often operate in GPS-denied environments. One example of a GPS-denied area might be along a river where the signal is blocked by a free canopy. Another might be inside a building or in a tunnel. It is understood that precision navigation improves squad level coordination and performance.

Typical GPS performance for dismounts is assumed to be accurate to 6 meters throughout this disclosure for illustration purposes only. Active sensors (e.g., radars) are usually not permitted for navigation use, since they increase squad vulnerably. Passive sensors (e.g., cameras) are subject to multiple challenges: lighting, occlusion, blur, expensive image processing. Additionally, squad members often have to carry heavy loads; therefore any navigation system with additional significant SWAP (size, weight and power) is not feasible. Such constraints on personal navigation options narrow the choice to low SWAP inertial navigation system (INS), which usually contains one or more of a 3-axial accelerometer, a 3-axial gyroscope and a 3-axial magnetometer. Unfortunately, the straightforward use of an INS is subject to time-in-cube drift in position, which results in small SWAP INS approach errors in meters within seconds.

Due to gyroscopic drift caused by very small tilts, a traditional INS cannot maintain positional accuracy for a human agent beyond a few seconds, as error grows as $O(t3)$. In certain embodiments, the system circumvents this error growth by mounting IMUs on boots and performing inertial navigation only during periods when the boot is actually in motion (e.g., about 0.5 seconds at a time during forward strides). When the boot is momentarily at rest between strides (the "stance phase"), zero-velocity updates (ZUPTs) are applied. In certain embodiments, the gyroscopes within the IMUs are able to stabilize, enabling reset of the IMU integration time. As a working prototype demonstrated, regular velocity resets effectively replaced $O(t3)$ error growth with a rate that increased linearly with the distance walked. Associated drift did not exceed 0.3% of the distance walked.

In one embodiment, an IMU applied to a dismount moving at 2 m/s suggested that location error would remain below 6 m (comparable to GPS performance) for ~16 minutes (equivalent to a 2 km distance). While boot-mounted IMUs may not be practical for the squad, boot-embedded IMUs have maintenance and logistical challenges. ZUPT may be ineffective for boot mounted IMUs when movements such as crawling and climbing occur because an individual's leg motions may not achieve the periodic stance phase.

Figure 10:
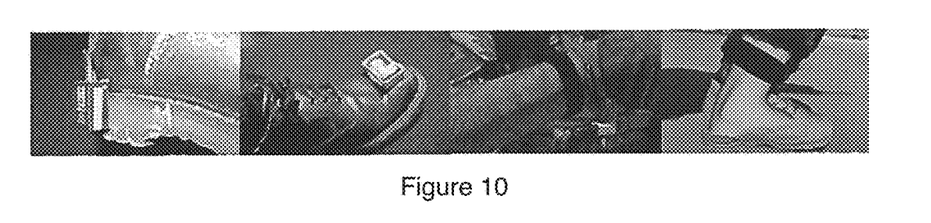
FIG. 10 shows possible mounting positions of IMUs of certain embodiments of the present disclosure.

Referring to FIG. 10, the left images show two mounting positions of the IMU tested. No obvious performance differences were reported; therefore it is anticipated that an anklet-mounted IMU (right) will provide comparable performance for walk-type movements (about 4 minutes stability versus 16 minutes for a shoe mount). In certain embodiments, MEMS IMU were used. In certain embodiments, a bracelet IMU (mid-right) complements an anklet for crawls and climbs.

In certain embodiments of the system of the present disclosure, maintenance and hardware challenges were overcome by employing two IMU bracelets deployed on the wrist and ankle. In one embodiment, (FIG. 10, right) the INS+ZUPT capability was applied to the entire range of operational movements of a human agent. Such ankle deployment is conceptually similar to that of a shoe mount. However, the stance phase may be shorter due to the possibility of rotation (pitch). This reduced the time interval during which position error stays below 6 meters.

Figure 11:
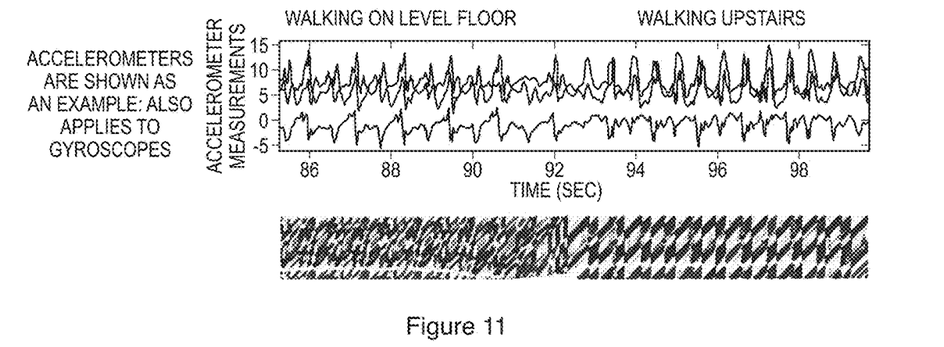
FIG. 11 shows a comparison of raw data (upper) and GDIs (lower) of a subject walking on a level floor and walking up stairs in one embodiment of the present disclosure.
Figure 12:
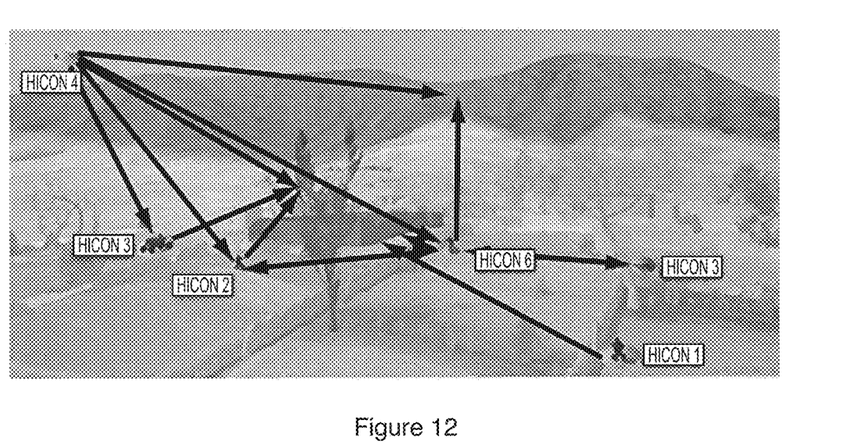
FIG. 12 shows one embodiment of a multi-agent joint navigation solution for squad operations according to the principles of the present disclosure.

FIG. 11 shows a comparison of raw data (upper) and GDIs (lower) of a subject walking on level floor and walking upstairs in one embodiment of the present disclosure. FIG. 12 shows one embodiment of a multi-agent joint navigation solution as used for squad operations. Here, GDIs can be used to map various terrain type transitions. Since GDIs are dynamically formed over a period of several seconds, transitioning from one terrain to another would result in significant changes in GDI structure, while staying on the same terrain would not have significant changes in GDI structure.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. Modifications and substitutions by one of ordinary skill in the art are considered to be within the scope of the present disclosure.

What is claimed:

1. A method of determining the position of a user comprising:
    providing one or more inertial measurement unit (IMU)/inertial navigation systems (INS) devices proximate to a user;
    collecting data from the one or more IMU/INS devices;
    creating signal processing representations from IMU/INS data, comprising:
        creating rotation and pace invariant gait dynamics images (GDI); and
        coupling the rotation and pace invariant GDIs with a land class database to identify a user's position relative to known land classes; and
    determining a relative position of the user.

2. The method of claim 1, wherein proximate to a user comprises proximate to a user's wrist or ankle.

3. The method of claim 1, further comprising
    comparing a user's position to apriori global coordinates update.

4. The method of claim 1, further comprising
    correcting the data from the one or more IMU/INS devices using zero velocity update (ZUPT) methodologies.

5. The method of claim 4, further comprising
    feeding the same IMU data into two processing channels, wherein the first channel comprises ZUPT corrected IMU/INS data for relative positioning and the second channel comprises signal processing representation terrain data for absolute positioning.

6. The method of claim 1, further comprising
    determining an absolute position of the user.

7. The method of claim 1, wherein the IMU/INS device is embedded in a user's clothing.

8. The method of claim 1, further comprising communicating the signal processing representations to an operator, where the operator uses the relative position of the user to monitor troop movement.

9. The method of claim 1, wherein the determining the relative position of the user comprises using the signal processing representations to determine a transition from a first land class to a second land class.

10. A method of tracking an individual on terrain types comprising:
    providing one or more IMU/INS devices proximate to a user;
    collecting data from the one or more IMU/INS devices;
    creating signal processing representations from IMU/INS data;

creating a land class descriptor using IMU/INS data from a user;
identifying an "on terrain type" signature; and
storing the "on terrain type" signature in a database.

11. The method of claim 10, wherein proximate to a user comprises proximate to a user's wrist or ankle.

12. The method of claim 10, wherein creating signal processing representations comprises creating rotation and pace invariant gait dynamics images (GDIs).

13. The method of claim 10, further comprising identifying a (latitude, longitude) pair with GPS information; and
comparing the GPS information with a land class database.

14. The method of claim 10, wherein the land class database comprises land class classifiers comprised of rotation and pace invariant GDIs.

15. The method of claim 10, wherein the database is accessed by a health care provider for use in treatment recommendations.

16. The method of claim 10, wherein the database is accessed by a user for use in modifying behavior.

17. The method of claim 10, further comprising communicating the signal processing representations to an operator, where the operator uses the relative position of the user to map an area.

18. The method of claim 10, wherein the IMU/INS device is embedded in a user's clothing.

19. The method of claim 10, wherein identifying an "on terrain type" signature comprises assigning a terrain's relative hardness.

* * * * *